United States Patent [19]
Dumont et al.

[11] Patent Number: 5,652,387
[45] Date of Patent: Jul. 29, 1997

[54] DEVICE FOR NON-DESTRUCTIVE ULTRASONIC TESTING OF A CYLINDRICAL WALL ACCESSIBLE THROUGH A NARROW ANNULAR PASSAGE

[75] Inventors: Pascal Dumont, Chatenoy le Royal; Damien Deltour, Essertenne, both of France

[73] Assignee: Framatome, Curbevoie, France

[21] Appl. No.: 549,714

[22] PCT Filed: Feb. 15, 1995

[86] PCT No.: PCT/FR95/00180

§ 371 Date: Feb. 28, 1996

§ 102(e) Date: Feb. 28, 1996

[87] PCT Pub. No.: WO95/25278

PCT Pub. Date: Sep. 21, 1995

[30] Foreign Application Priority Data

Mar. 17, 1994 [FR] France .................... 94 03154

[51] Int. Cl.⁶ .................... G01N 29/10; G01N 29/24
[52] U.S. Cl. .................... 73/622; 376/249; 73/624
[58] Field of Search .................... 376/249, 245, 376/250, 290; 976/DIG. 236, DIG. 212; 73/622, 624, 628, 641, 640, 632, 623

[56] References Cited

U.S. PATENT DOCUMENTS

| | | | |
|---|---|---|---|
| 4,330,865 | 5/1982 | Hyde et al. | 376/249 |
| 4,368,642 | 1/1983 | Carodiskey | 73/623 |
| 4,472,346 | 9/1984 | Takeda et al. | 376/246 |
| 4,569,230 | 2/1986 | Asty et al. | 73/623 |
| 5,156,803 | 10/1992 | Engding et al. | 376/249 |
| 5,327,079 | 7/1994 | Haller et al. | 324/219 |
| 5,436,944 | 7/1995 | Magnin et al. | 376/249 |

FOREIGN PATENT DOCUMENTS

| | | |
|---|---|---|
| 289 207 | 4/1988 | European Pat. Off. |
| 29 13 742 | 10/1980 | Germany . |
| 3508415 | 9/1986 | Germany . |
| 2 198 532 | 6/1988 | United Kingdom . |

Primary Examiner—Hezron E. Williams
Assistant Examiner—Rose M. Miller
Attorney, Agent, or Firm—Pollock, Vande Sande & Priddy

[57] ABSTRACT

The device includes a blade (1), one end of which carries a testing probe (2). The probe (2) includes a first ultrasonic transducer (23) constituting an emitter and a second ultrasonic transducer (24) constituting a receiver, which are pivotably mounted at the end of the blade (1) about two axes parallel to the longitudinal direction of the blade (1), arranged separated from one another in the transverse direction of the blade (1), so as to be placed in a narrow annular passage, in contact with a cylindrical wall to be tested, in two positions separated from one another in a circumferential direction of the annular passage.

14 Claims, 3 Drawing Sheets

DEVICE FOR NON-DESTRUCTIVE ULTRASONIC TESTING OF A CYLINDRICAL WALL ACCESSIBLE THROUGH A NARROW ANNULAR PASSAGE

The invention relates to a device for non-destructive ultrasonic testing of a surface accessible through a narrow annular passage. The invention may be applied in particular to the non-destructive testing of the inner surface of a tubular adaptor passing through the vessel head of a pressurized water nuclear reactor, without removing the thermal sleeve of the adaptor.

Pressurized water nuclear reactors generally include a vessel containing the core of the reactor which is immersed in the pressurized water for cooling the reactor.

The generally cylindrical vessel includes a hemispherical head which may be attached to its upper part. The head is pierced with openings, at each of which a tubular penetration part is fastened by welding, constituting an adaptor allowing passage and displacement control of a follower of a rod cluster for controlling the reactivity of the core or a through-passage for a means for measurement inside the core, such as a thermocouple column.

The mechanisms for controlling displacement of the core reactivity control rod clusters are fixed on the end parts of the adaptors.

A heat sleeve is fixed inside each of the tubular penetrations of the vessel head, in a coaxial arrangement with respect to the tubular penetration part and with some radial clearance, which thermal sleeve includes a diametrally widened part located at the upper part of the bore of the tubular penetration part and is mounted freely in rotation inside the penetration.

The nuclear reactor reactivity control rod followers and thermocouple columns pass through the vessel head inside thermal sleeves which are themselves arranged coaxially inside control rod adaptors or more generally inside tubular head penetration parts.

So as to increase the reliability and safety of operation of nuclear reactors and in order to extend their lifetime, operators have to carry out increasingly numerous tests on the various elements constituting the nuclear reactor.

In particular, it may be necessary to test the condition of the vessel head penetration parts in order to ensure integrity of these parts after a certain length of operation of the reactor, in particular in the zone in which these tubular parts are welded on the vessel head.

These tests, which make it possible to detect and repair faults on the cylindrical inner surface of the tubular penetration part, must be carried out through the inside of the bore of the tubular part and may consequently require removal of the thermal sleeve in order to access the inner surface of the bore of the penetration.

The tests and repairs are carried out during a shutdown of the nuclear reactor, the vessel head being removed and placed on a maintenance stand.

Removing the thermal sleeve requires complex operations insofar as the widening of the thermal sleeve resting on a bearing surface arranged at the upper part of the adaptor prevents removal of the sleeve by pulling downwards on its lower part which is accessible below the head.

Furthermore, neither is it possible to remove the sleeve by pulling upwards insofar as the rod cluster control mechanisms which are fixed by screwing and welding on the upper parts of the adaptors prevent passage of the thermal sleeve.

It is therefore desirable to limit the complex thermal sleeve removal operations to adaptors which actually exhibit defects requiring repair.

In Patent Applications FR-A-92.15788 and 92-15789 filed by the company FRAMATOME, a device is described for testing the internal surface of an adaptor, comprising a blade, deformable in flexion, carrying a testing probe at one of its ends and means for moving the testing probe fixed to the end of the blade inside the narrow annular space between the thermal liner and the inner surface of an adaptor. The blade is preferably made in the form of a laminated strip which absorbs vibrations, and the testing probe by an eddy-current sensor.

It is also envisaged, by way of a variant, to use an ultrasonic sensor for detecting the possible presence of cracks and for measuring their depth inside the adaptor.

However, it has been shown that the use of an eddy-current sensor does not allow very precise determination of the location, the geometrical shape and above all the dimensions of the cracks detected on the inner surface of the adaptor.

In order to determine the seriousness of the cracks detected and their effect on the operation of the nuclear reactor as well as the possibility and the ways of repairing the cracks, it is necessary to determine the dimensions of these cracks and in particular their dimension in the direction of the thickness of the tubular adaptor.

The known non-destructive testing means of the prior art do not allow optimal characterization and measurement of the cracks of parts such as an adaptor accessible solely through a narrow annular space.

The object of the invention is therefore to provide a device for non-destructive ultrasonic testing of a cylindrical wall accessible through a narrow annular passage in the radial direction of the cylindrical wall, including a blade whose thickness is less than the radial width of the annular passage carrying at least one testing probe in the vicinity of one of its ends, this device making it possible to measure, locate and determine defects such as cracks in the cylindrical wall.

For this purpose, the probe includes a first ultrasonic transducer constituting an emitter and a second ultrasonic transducer constituting a receiver, which are pivotably mounted at the end of the blade about two axes parallel to the longitudinal direction of the blade, arranged separated from one another in the transverse direction of the blade, so as to be placed in the annular passage in two positions separated from one another in a circumferential direction of the annular passage.

In order better to explain the invention, a description will now be given, by way of non-limiting example, of a testing device according to the invention and according to several alternative embodiments and its use for testing the inner surface of a pressurized water nuclear reactor vessel head penetration adaptor.

Figure 1:
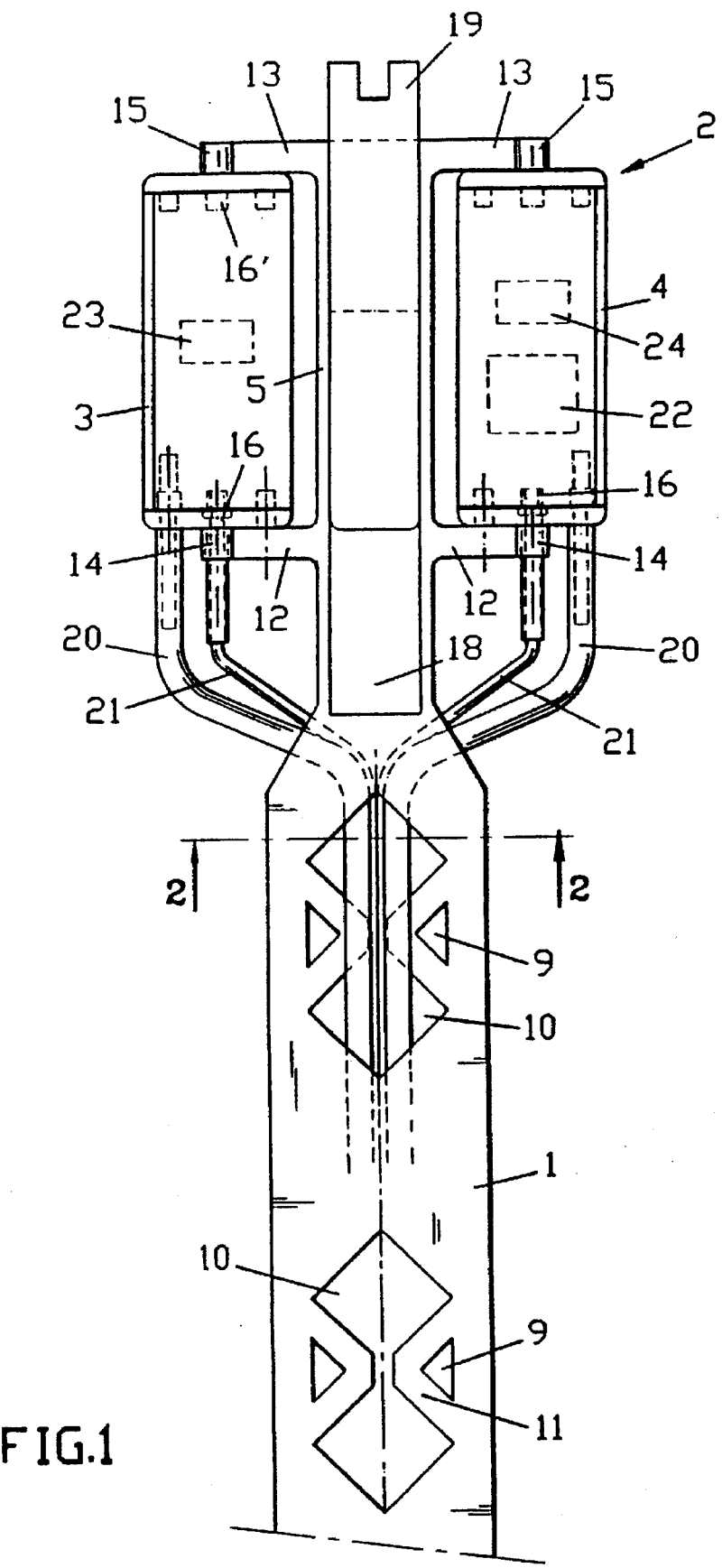
FIG. 1 is a view in elevation of the end part, carrying the testing probe, of the blade of a testing device according to the invention in position in the annular passage between the inner surface of an adaptor and the thermal sleeve.

FIG. 1 shows an end part of a steel blade 1 of a testing device according to the invention, carrying the ultrasonic testing and measurement head 2. The testing head 2 includes two ultrasonic transducer supports 3 and 4 mounted on a support 5 at the end of the blade 1.

Figure 2:
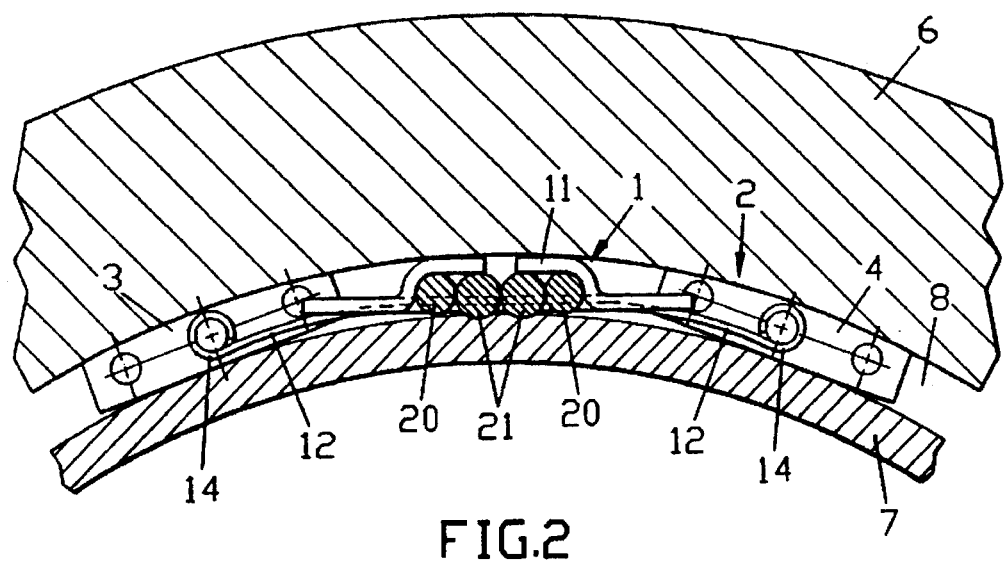
FIG. 2 is a view in the longitudinal direction of the blade, along 2—2 in FIG. 1, of the end of the blade and of the testing probe in the working position in the annular passage.

As can be seen in FIG. 2, the measurement head 2 including the transducer supports 3 and 4 can be introduced and moved by the blade 1 in a narrow annular passage 8 in the radial direction, between the inner surface of an adaptor 6 and the outer surface of a thermal sleeve 7, coaxial with the adaptor 6.

It is possible to use, for example, a device as described in FR-A-92-15788, for introducing and moving the blade and the measurement head 2 inside the annular passage, in order to carry out the testing of the inner surface of the adaptor, for example at the level where it is welded to the vessel head.

Figure 3:
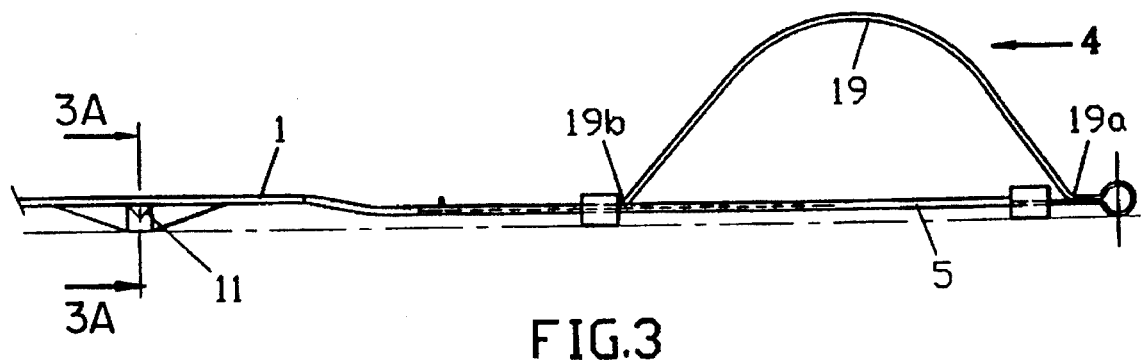
FIG. 3 is a side view of the end of the blade constituting the support for the testing probe of the device represented in FIGS. 1 and 2.
Figure 3A:
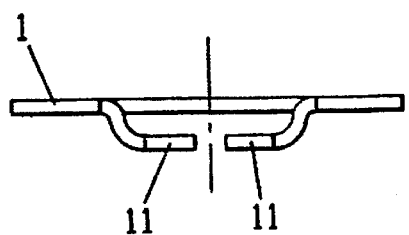
FIG. 3A is a cross-sectional view along A—A of FIG. 3.

The blade 1 includes cut-outs such as 9 and 10 regularly spaced along its longitudinal direction, between which tabs 11 are made which can be shaped by folding to have a part in a plane parallel to the plane of the blade 1, as represented in FIGS. 2, 3 and 3A, for guiding and holding the blade in the annular space 8.

Figure 4:
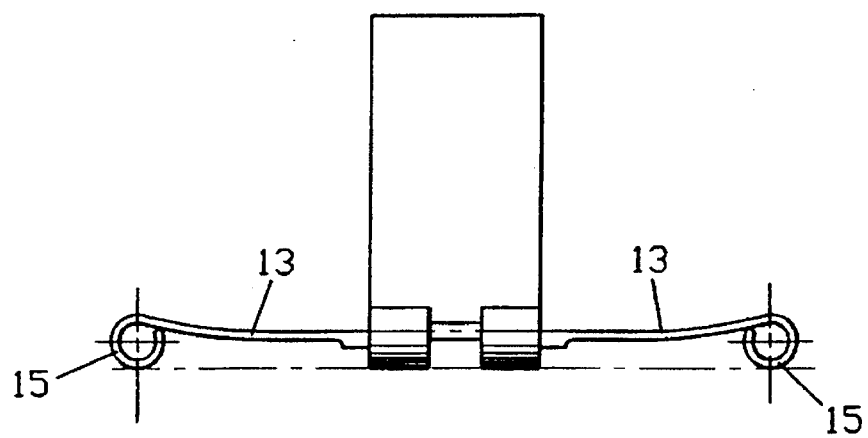
FIG. 4 is a front view along 4 in FIG. 3.

The support 5 of the measurement head 2 on which the transducer holders 3 and 4 are mounted includes two pairs of arms 12, 13 in transverse directions substantially perpendicular to the longitudinal direction of the blade 1, which arms consist of elastic spring blades whose outer end part is rolled to form two pairs of loops 14 and 15 visible in FIGS. 2 and 4.

The blade 1 may have a thickness of the order of 0.5 mm. In preference, the arms of the support of the transducer holders are thin compared with the body of the blade, with a possible thickness of the order of 0.25 mm.

The transducer support 3 is pivotably mounted about an axis parallel to the longitudinal axis of the blade, by means of two pivots 16 and 16' engaged inside the loop-shaped end parts of an arm 12 and of an arm 13 which are aligned along the longitudinal direction of the blade.

Similarly, the transducer holder 4 is pivotably mounted about an axis parallel to the longitudinal axis of the blade, by means of two pivots 17 engaged in the loop-shaped end parts 14 and 15 of the other two arms 12 and 13 which are aligned along a longitudinal direction of the blade 1.

The pivot axes of the two transducer holders 3 and 4, parallel to the longitudinal direction of the blade 1, are spaced apart from one another in a direction which is transverse with respect to the blade and are arranged equidistant from either side of the longitudinal mid-axis 18 of the blade 1, because they are fixed to the end of the transversely oriented arms 12 and 13.

The central part of the support 5 carries a curved pressing spring 19 obtained by forming, one end 19a of which is held in position by welding on a face of the support 5 of the blade and the second end 19b of which is free and can be moved by sliding over the support 5. The spring 19 has a convex surface pointing away from the face of the support 5.

When the measuring head 2 is introduced into the annular passage 8 to come into the testing position, as represented in FIG. 2, the curved blade of the return spring 19 comes into contact via its outer convex part with the outer surface of the thermal sleeve 7 and undergoes bending with sliding of the end 19b over the surface of the support 5. Because of the bending, the curved blade of the spring 19 exerts a return force in the radial direction of the adaptor 6 and of the sleeve 7, pressing the testing and measuring head 2 of the probe against the inner wall of the adaptor 6. The return force in the direction of the inner surface of the adaptor 6 is transmitted to the transducer holders 3 and 4 via the elastic arms 12 and 13, so that the transducer holders 3 and 4 are completely pressed against the inner surface of the adaptor 6 on which the test is carried out.

As can be seen in FIG. 2, the outer surfaces of the transducer holders 3 and 4 have a curvature similar to the curvature of the inner surface of the adaptor 6, in order to ensure perfect contact between the transducer holders and the surface to be tested.

Furthermore, the arms 12 and 13, constructed in the form of thin elastic leaf springs can adopt, under the effect of the return force exerted by the spring 19, a curvature identical to the curvature of the annular space 8. Positioning of the transducer holders 3 and 4 in a position completely pressed against the inner surface of the adaptor 6 is made possible by virtue of the pivoting mounting of these transducer holders at the end of the arms 12 and 13. Because of this, the transducer holders 3 and 4 can be oriented perfectly along the direction of the cylindrical inner wall of the adaptor 6.

Each of the transducer holders 3, 4 is furthermore connected to the end of a pipe 20 making it possible to supply a coupling liquid such as water in a zone neighbouring the internal wall part of the adaptor 6 on which the test is carried out.

The pipes 20 consist of tubes fixed to the blade 1 in a longitudinal direction and comprising end parts which are folded outwards so as to be engaged on end-pieces integral with the supports 3 and 4. The tubes 20 are sufficiently flexible to be folded and engaged on the connection end-pieces of the transducer holders 3 and 4 and to accompany the pivoting of the transducer holders 3 and 4 with respect to the support 5 when positioning the testing head 2. The tubes 20 are nevertheless sufficiently rigid to hold the transducer holders 3 and 4 in a position facilitating their introduction in the annular passage 8.

The transducer holders 3 and 4 are also connected, at the pivots 17 and 16, to electrical conductors 21 also carried by the blade 1 and arranged in a longitudinal direction on the blade 1, as far as their end parts which are connected to the transducer holders at the pivots 16 and 17.

The coupling-liquid supply tubes 20 and the conductors 21 are connected to the transducer holders via special connectors for coaxial cables.

The electrical conductors 21 are connected, via connectors, to ultrasonic transducers 23 and 24 mounted on the transducer holders 3 and 4 respectively.

The ultrasonic transducer 23 is supplied with electric current through one of the conductors 21 and constitutes an emitter. The second ultrasonic transducer 24, mounted on the transducer holder 4, is connected to a conductor 21 via a preamplifier 22 and constitutes a receiver collecting the measurement signals which are transmitted to an interpretation unit by the electrical conductor 21, after amplification in the preamplifier 22.

In preference, the emitter is made of a piezoelectric ceramic-based composite or ceramic, and the receiver a piezoelectric polymer or copolymer having the structure and properties of a plastic sheet.

In fact, this combination makes it possible to obtain very good conditions, both of emission and reception of ultrasound.

However, the materials may be of the same nature and expediently chosen so as to obtain equivalent sensitivity in emission or reception in order to be able to use the transducers equally well as emitters or as receivers.

It is possible, for example, to use ceramic-based piezo-composites as piezoelectric emission and reception elements. Such elements consist of rods, cut out from a block of ceramic with a thickness of the order of 50 μm, which are then embedded in a polyurethane-based polymer material.

The two faces of the elements are made level and then metallized.

Figure 5:
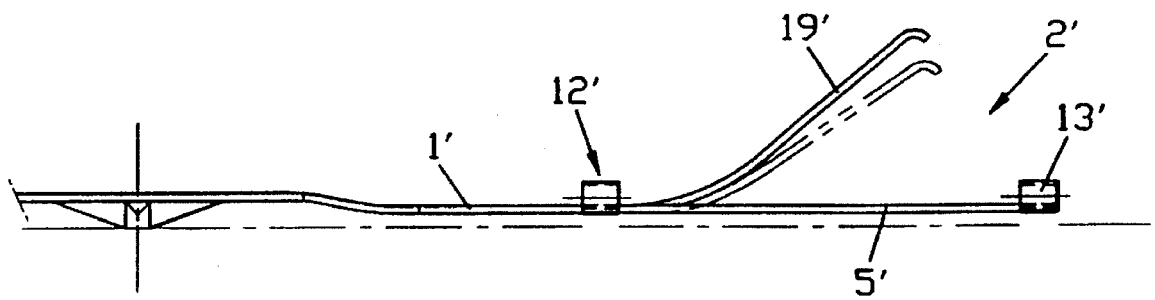
FIG. 5 is a side view, similar to the view of FIG. 3, of a probe support blade according to an alternative embodiment.

FIG. 5 represents an alternative embodiment 1' of a blade of a testing device according to the invention.

The end part 5' of the blade 1' constituting the support of the transducer holders which includes transversely directed arms 12' and 13' for pivotal mounting of the transducer holders includes a return spring 19', fixed to its central part, which consists of a single curved blade which is raised with respect to the surface of the blade so that its end, when unstressed, is at a certain distance from the support 5' of the blade.

When the measuring head 2' constituting the end part of the blade 1' is introduced into the annular passage giving access to the surface of the adaptor to be tested, the spring 19' undergoes bending towards the surface of the support 5' and exerts a return force in the radial direction of the adaptor, like the spring 19' represented in FIG. 3, the end 19b of which is mounted slidingly on the support surface 5'.

Although the embodiment of the support 19' in the form of a single curved blade has advantages as regards its ease of production, compared with a curved spring 19 as represented in FIG. 3, the blade 19' may catch and become folded when it is introduced into the tubular passage. This risk does not exist with the curved blade 19 whose shape is represented in FIG. 3.

Figure 6:
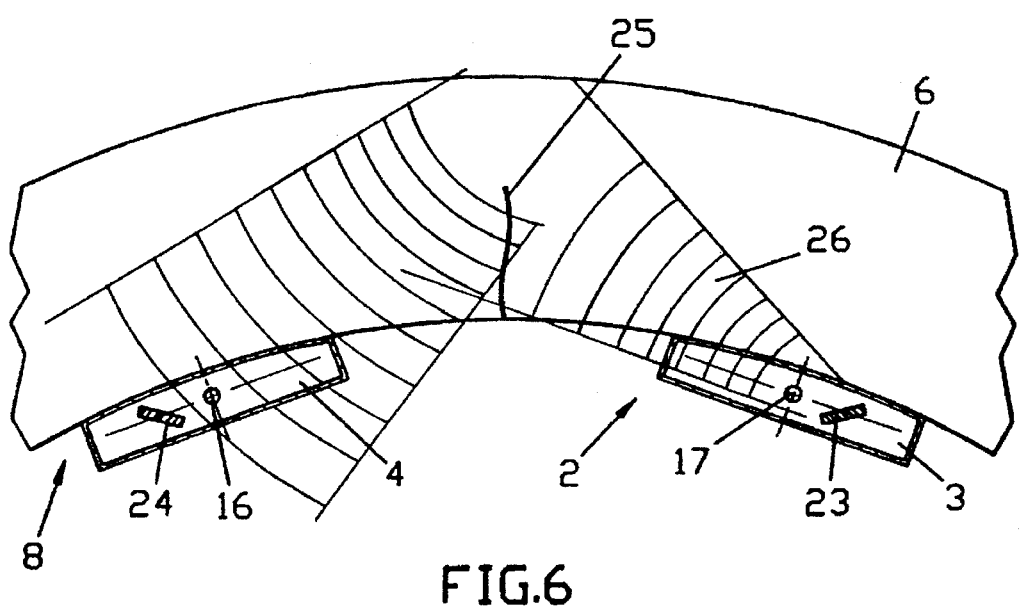
FIG. 6 is a large-scale diagrammatic view, similar to the view in FIG. 2, of the measurement probe of a device according to the invention in the working position level with a crack in the wall of a pressurized water nuclear reactor vessel head penetration adaptor.

FIG. 6 shows the testing head 2 of a testing device according to the invention in position for testing a part of the inner surface of an adaptor 6 which has a crack 25 in a substantially radial direction and over a large part of the thickness of the wall of the adaptor 6.

This testing position may be obtained during the movement of the testing head 2 in translation along the axial direction and in rotation of the head 2 inside the annular passage 8, for example by using a device, as described in Patent Application FR-A-92-15788, for moving the blade of the testing device.

In the position of the testing head 2 shown in FIG. 6, the transducers 23 and 24 fixed on the transducer holders 3 and 4 respectively are in substantially symmetrical arrangements with respect to the crack 25.

The transducer 23, which is supplied with electric current, produces an ultrasonic beam 26 which is emitted towards the crack 25. The beam 26 is received, after reflection, by the transducer 24 which produces signals representing the characteristics of the crack 25, which are amplified by the preamplifier 22 then sent via the conductors 21 to a processing unit.

The arrangement of the two transducers substantially symmetrically on either side of the crack 25 makes it possible to obtain signals which can be interpreted in order to make dimensional measurements of the crack 25.

In particular, it is possible to determine the penetration depth of the crack 25 in the wall of the adaptor 6.

The fact that the two transducers are separated from one another in the circumferential direction of the annular space 8 makes it possible to carry out a complete scan of the crack 25 with the ultrasonic beam so as to allow dimensioning of the crack in the direction of the thickness of the wall of the adaptor.

The testing device according to the invention therefore makes it possible to position the testing probe including an ultrasonic emitter transducer and receiver transducer so as to make it possible to examine, under very good conditions, a cylindrical surface such as the inner surface of an adaptor, from a very narrow annular space in contact with this cylindrical surface. This result is obtained by virtue of the use of transducer supports pivotably mounted about axes having a longitudinal direction parallel to the axis of the cylindrical surface.

Furthermore, the fact of using an emitter transducer and a receiver transducer which are spaced apart from one another along a circumferential direction of the cylindrical surface during testing makes it possible to carry out a complete scan of the wall to be examined and dimensioning of the defects present in this wall, which is not possible when a single ultrasonic transducer is used, placed in a testing position in radial alignment with the crack.

The invention is not limited to the embodiments which have been described.

Thus, the transducer holders may have a different arrangement from that which has been described and the support consisting of the end part of the blade may be produced in a different manner from that which has been described.

The elongate blade constituting the part of the arrangement allowing positioning of the probe and its movement along the surface to be tested may have a different structure from that which has been described.

The movement of the probe via the blade may be carried out by any means other than those described in Patent Application FR-A-92-15788.

Furthermore, it is possible to use a testing head at the end of the blade having more than two transducer holders and transducers.

It is possible, for example, to use three or four transducer holders, themselves carrying one or more transducers which can be used as emitters or receivers.

The arrangement of the preamplifier integrated with the transducer holders on which the receiver is fixed allows a high gain in the intensity of the measurement signal, it being possible for this gain to be of the order of 30 dB. However, it is also possible not to use a preamplification stage integrated with the transducer holder on which the receiver is mounted.

In the case when use is made of piezo-composite elements which may be emitters or receivers, a two-channel emitter/receiver preamplifier is associated with each one of them.

The two channels of the preamplifier must be balanced in power in order to ensure operation in emission and in reception.

It is thus possible, by switching over the emitter and receiver functions of two elements of a probe, to test the wall of the adaptor with two directions of propagation of the ultrasound waves, in a single pass of the probe.

The transducer holders may have any structure, it being possible for the transducers to be fixed on the transducer holders by any means, for example by adhesive bonding or mechanical fastening.

The blade of the device, at the end of which the measuring head is fixed, is preferably made of austenitic stainless steel.

It is obvious that the various components listed hereinabove may be produced in an equivalent manner by other means, the person skilled in the art being capable of adapting the design and construction of the device to the testing operation to be carried out.

The invention applies not only to testing the inner surfaces of adaptors but to the testing of any concave or convex cylindrical surface which is accessible only through a narrow space in the radial direction of the cylindrical surface, it being possible for this narrow space in contact with the surface to be tested to have an annular shape or another shape.

Finally, the device according to the invention may be applied very broadly in the field of testing apparatuses or installations which include, in particular, cylindrically shaped tubular parts.

We claim:

1. Device for non-destructive ultrasonic testing of a cylindrical wall accessible through an annular passage, of narrow width in the radial direction of the cylindrical wall, including a blade whose thickness is less than the width of the annular passage in the radial direction, carrying at least one testing probe in the vicinity of one of its ends, wherein the probe includes a first ultrasonic transducer constituting an emitter and a second ultrasonic transducer constituting a receiver, which are pivotably mounted at the end of the blade about two axes parallel to the longitudinal direction of the blade, arranged separated from one another in the transverse direction of the blade, so as to be placed in the annular passage in two positions separated from one another in a circumferential direction of the annular passage.

2. Device according to claim 1, wherein the first ultrasonic transducer is fixed on a first transducer holder pivotably mounted on a support arranged at the end of the blade and in that the second transducer is fixed on a second transducer holder pivotably mounted on the support at the end of the blade.

3. Device according to claim 2, wherein the support comprises the end part of the blade which includes two pairs of arms substantially perpendicular to the longitudinal direction of the blade, which consist of elastic spring blades comprising, at outside ends, parts wound in the shape of loops for receiving pivots of the transducer holders.

4. Device according to claim 2, wherein the support also includes a spring for returning the support, inside the annular space, in a radial direction of the cylindrical wall.

5. Device according to claim 4, wherein the return spring has the shape of a curved blade having an end integral with a face of the support of the blade, an end mounted slidingly over the surface of the support and a convex part pointing outwards with respect to the face of the support.

6. Device according to claim 4, wherein the return spring consists of a curved blade having an end fixed on a face of the support and a free end away from the face of the support.

7. Device according to claim 1, wherein the first transducer, used an as emitter, is made of material containing a piezoelectric ceramic and in that the second transducer, used as a receiver, is made of a material containing a piezoelectric polymer.

8. Device according to claim 1, wherein the first and second transducers are both made of a piezo-composite material and are capable of being used as emitter and as receiver.

9. Device according to claim 2, wherein that a preamplifier is fixed on the second transducer holder and connected to the second transducer for amplifying the measurement signals received by the second transducer.

10. Device according to claim 8, wherein a two-channel preamplifier is associated with each of the first and second transducers.

11. Device according to claim 2, wherein at least one coupling-liquid supply tube and at least one electrical conductor are connected to each of the transducer holders for supplying the test zone with coupling liquid, electrically supplying the first emitter transducer and collecting the measurement signals from the receiver transducer.

12. Device according to claim 11, wherein the coupling-liquid supply pipes and the electrical conductors are fixed on the blade along its longitudinal direction and include an end connected to one of the transducer holders which separates transversely from the longitudinal direction of the blade.

13. Device according to claim 11, wherein the pipes and the conductors are connected to the transducer holders via connectors for coaxial cables.

14. Device according to claim 1, wherein the blade includes cut-outs defining tabs which are folded so as to include a part in a plane parallel to the plane of the blade for guiding and holding the blade in the annular passage.

* * * * *